United States Patent
Beyersdorf

(10) Patent No.: US 6,306,113 B1
(45) Date of Patent: *Oct. 23, 2001

(54) REPERFUSION DEVICE

(76) Inventor: Friedhelm Beyersdorf, Talvogtei 6b, D-79199 Kirchzarten (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/013,131

(22) Filed: Jan. 26, 1998

(30) Foreign Application Priority Data

Jan. 24, 1997 (DE) .............................. 197 02 402

(51) Int. Cl.⁷ .......................... A61M 37/00; A61M 5/00; A61M 1/00; A61M 31/00; B65D 35/28
(52) U.S. Cl. .......................... 604/4.01; 604/7; 604/5.01; 604/30; 604/65; 604/67; 604/407; 222/95
(58) Field of Search .................. 604/4, 5, 403, 604/4.01, 5.01, 6.1, 6.01, 6.15–6.16, 6.11, 7, 266, 407–409, 28–31, 34, 48, 65–67; 210/650, 645; 222/95; 427/2.3

(56) References Cited

U.S. PATENT DOCUMENTS

| | | | |
|---|---|---|---|
| 4,259,952 | 4/1981 | Avoy ..................... | 128/214 |
| 4,336,802 | 6/1982 | Stone et al. ............. | 128/272 |
| 5,234,403 | * 8/1993 | Yoda et al. ............. | 604/4.01 |
| 5,286,388 | * 2/1994 | Ingram ................... | 210/650 |
| 5,322,500 | 6/1994 | Johnson et al. .......... | 604/4 |
| 5,380,314 | * 1/1995 | Herweck et al. ......... | 604/403 |
| 5,464,650 | * 11/1995 | Berg ..................... | 427/2.3 |
| 5,496,303 | 3/1996 | Antonetti ............... | 604/410 |
| 5,497,912 | * 3/1996 | Hoback .................. | 222/95 |
| 5,533,957 | * 7/1996 | Aldea . | |
| 5,573,502 | * 11/1996 | LeCocq et al. . | |
| 5,702,818 | * 12/1997 | Cahalan et al. .......... | 428/409 |
| 5,800,374 | 9/1998 | Beyersdorf .............. | 604/4 |
| 5,955,588 | * 9/1999 | Tsang et al. ............ | 536/21 |

FOREIGN PATENT DOCUMENTS

| | | |
|---|---|---|
| 4001086 | 7/1991 | (DE) . |
| 4003425 | 8/1991 | (DE) . |
| 096215 | 12/1983 | (EP) . |
| 0210424 | 4/1987 | (EP) . |
| 0633031 | 11/1995 | (EP) . |
| 95 17134 | 6/1995 | (WO) . |

* cited by examiner

Primary Examiner—Angela D. Sykes
Assistant Examiner—Patricia M Bianco
(74) Attorney, Agent, or Firm—Ostrolenk, Faber, Gerb & Soffen, LLP

(57) ABSTRACT

A reperfusion device for reperfusion of a blood vessel. Blood is withdrawn from a patient and is metered into a first compressible bag. The first bag is connected with a second compressible bag. Compression of the first bag transfers blood from the first bag to the second bag. The second bag is connected with a supply container for metered supply of reperfusion liquid which is mixed with the blood that enters the second bag. The mixture of blood and reperfusion liquid is transferred in a metered amount from the second bag through a reperfusion catheter into a blood vessel by compressing the second bag. The bags are compressed either manually or by a respective pressure cuffs. Hose clamps are provided on the tubing between the bags and on the reperfusion catheter. Meters measure and indicate the flow into and out of each of the bags and through the reperfusion catheter.

11 Claims, 2 Drawing Sheets

REPERFUSION DEVICE

BACKGROUND OF THE INVENTION

1. Field of the Invention

The present invention relates to a method for mixing blood and an auxiliary liquid for reperfusion of blood vessels and also relates to a reperfusion device.

2. Description of the Related Art

DE 3,820,840 C1 discloses an aqueous reperfusion solution for preventing reperfusion damage following acute, peripheral vessel obstruction in a patient. EP 0,513,071 B1 discloses a reperfusion device for reperfusion of blood vessels. That device has the following features: a catheter which can be introduced into a blood vessel, a blood withdrawal device for withdrawing oxygenated arterial blood from a patient, means for mixing a reperfusion solution with the blood withdrawn from the patient, a mechanical pump device for delivering the mixture of blood and reperfusion solution through the catheter into the blood vessel, and pressure measurement means arranged at the tip of the catheter and in the form of a pressure measurement lumen or a pressure probe. Various methods are known for eliminating blood vessel obstructions. However, despite successful restoration of the blood flow, the morbidity and mortality rates are still relatively high after such a vascular intervention. The main reason for this is reperfusion damage, i.e., a tissue lesion which occurs upon the vessel obstruction being eliminated, if the blood starts to flow through the artery again at the full arterial pressure generated by the heart. This disadvantage is avoided or is substantially reduced by using the reperfusion solution, after the vessel obstruction has been eliminated. This reperfusion solution is introduced, for example by using a reperfusion device, into the vessel over a longer period of time, e.g. over 30 minutes, and at a reduced pressure, before the vessel is once again loaded with the full arterial pressure.

SUMMARY OF THE INVENTION

The object of invention is to perform reperfusion using means which are less expensive and easier to handle than known methods and devices.

In a reperfusion device for reperfusion of a blood vessel, blood is withdrawn from a patient and is metered into a first compressible bag. The first bag is connected with a second compressible bag. Compression of the first bag transfers blood from the first bag to the second bag. The second bag is also compressible and is connected with a supply container for metered supply of reperfusion liquid which is mixed with the blood that enters the second bag. The mixture of blood and reperfusion liquid is transferred in a metered amount from the second bag through a reperfusion catheter into a blood vessel by compressing the second bag. The bags are compressed either manually or by respective pressure cuffs. Hose clamps are provided on the tubing between the bags and on the reperfusion catheter. Meters measure and indicate the flow into and out of each of the bags and through the reperfusion catheter.

The invention provides a method and a device, and particularly provides a set of components for reperfusion, particularly for reperfusion of a patient's leg. The set is more acceptable for vascular surgery than are previously known means, because of low production costs and ease of handling. In principle, the set involves the use of two bags. The first bag is filled with blood from the iliac artery. This blood is then conveyed into the second bag, into which a defined amount of a reperfusion liquid had been placed earlier. This mixture of blood and reperfusion liquid is then passed into the leg artery over a predetermined period of time and at a pre-determined pressure selected so as to avoid producing a lesion in the vessel. This procedure is repeated several times. This is done without use of a pump, because each bag is compressed directly by hand or indirectly via a compressed air cuff which is operated by hand. The blood pressure is measured either in the delivery line from the second bag to the leg or in a delivery cannula which introduces mixture into the leg artery. Depending on the pressure value of the blood in the leg artery, the pressure in the delivery line is regulated by exerting greater or lesser pressure on the second bag. Since no heparin is provided in this treatment, all bags, tubings, catheters and other elements coming into contact with the blood, or with the mixture of blood and reperfusion liquid, must be equipped with a heparin coating.

Other features and advantages of the present invention will become apparent from the following description of the invention which refers to the accompanying drawings.

DETAILED DESCRIPTION OF THE INVENTION

Figure 1:
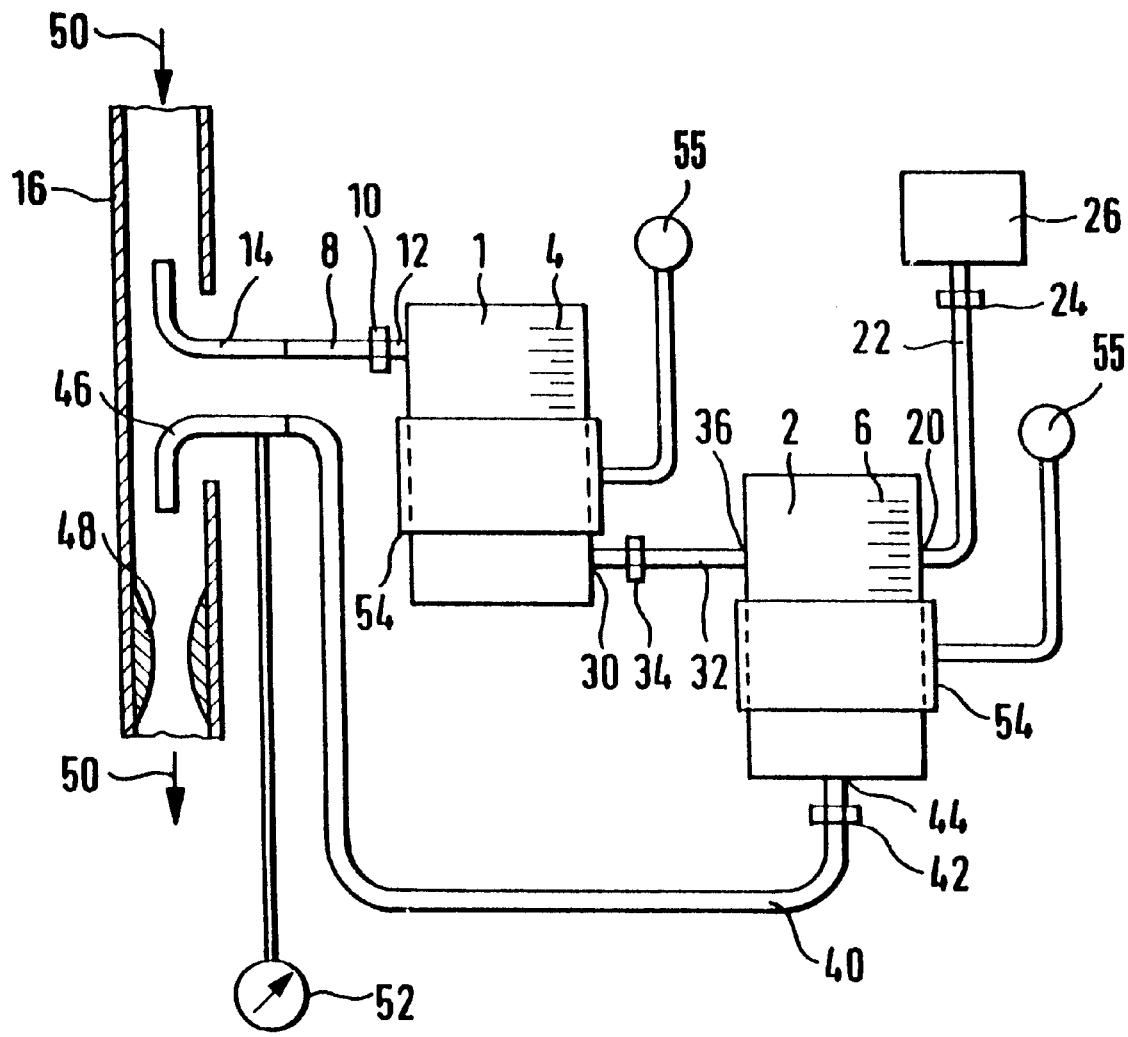
FIG. 1 is a diagrammatic representation of a set or a device for reperfusion according to the invention.

The set represented in FIG. 1 is used for reperfusion of blood vessels. It includes two commercially available and flexible bags 1 and 2 which can be manually compressed and are made of transparent or at least translucent, pliable material. Each has at least one filling level marker 4 or 6. Since the bags are transparent or at least translucent, an operator is able to detect whether the level of liquid in the bags has already reached a desired height relative to the marker 4 or 6.

The first bag 1 has a blood withdrawal tube 8 which can be alternately closed or opened via a closure element 10, preferably a hose clamp. The tube connects an inlet 12 of the bag 1, in the upper area of the bag, to a blood withdrawal catheter 14. The blood withdrawal catheter 14 is inserted into a schematically represented artery 16 of the patient so that blood pressure in the artery delivers blood to the first bag 1 up to the level of the desired marker 4 when the closure element 10 is opened.

An inlet 20 at the upper end section of the second bag 2 is connected via a reperfusion liquid delivery tube 22 to a container or reservoir 26 for the reperfusion liquid. The tube 22 can be alternately opened or closed via a closure element 24, preferably a hose clamp. By opening the closure element 24, reperfusion liquid can fill the second bag 2 until the reperfusion liquid in the second container 2 has reached a predetermined level of the height marker 6.

An outlet 30 at the lower end of the first bag 1 is connected to a second inlet 36 at the upper end section of the second bag 2 via a connection tube 32 which can be alternately closed or opened via a closure element 34, preferably a hose clamp. Thus, when the blood withdrawal tube 8 and the delivery tube 22 for reperfusion liquid are closed by their closure elements 10 and 24, respectively, a metered amount of the blood can be transferred from the first container 1 into the second container 2 and can be mixed there with the previously metered amount of reperfusion liquid when the closure element 34 of the connection tubing 32 is opened. The metered amount of blood to be transferred is preferably the amount which was previously removed from the artery 16 into the first bag 1 up to the predetermined height marker 4.

A reperfusion tube 40 can be alternately closed or opened at its upstream end via a closure element 42, preferably a hose clamp. The tube 40 is connected at its upstream end to an outlet 44 at the lower end of the second bag 2. It has a reperfusion catheter 46 at its downstream end, which can be inserted into the same artery 16 or into another artery of the same patient upstream of the site at which a vessel constriction or a vessel obstruction 48 has been earlier eliminated. The direction of flow of the arterial blood is represented by arrows 50. Thus, by opening the closure element 42 of the reperfusion tubing 40 after the closure elements 24 and 34 of the delivery tubing 22 for reperfusion liquid and of the connection tubing 32 have been previously closed, the previously metered amount of blood and reperfusion liquid can be delivered from the second container 2, through the reperfusion catheter 46 and into the artery, and indeed at a predetermined pressure and for a predetermined period of time.

The delivery pressure is visually displayed by a pressure measurement unit 52 which is connected to the delivery tubing 40 for reperfusion liquid or, preferably, is connected directly on the reperfusion catheter 46, and indicates the pressure therein. The period of time during which the mixture of blood and reperfusion liquid is introduced into the blood vessel, such as the artery 16, can be read off by an operator on any desired timepiece and can amount, for example, to about 30 minutes or so.

To empty blood from the first container 1 into the second container 2, the first container 1 is compressed by an operator. In the same way, to empty the mixture of blood and reperfusion liquid from the container 2 into the artery 16, the container 2 is compressed by an operator. The two bags 1 and 2 can be compressed manually, either by the operator's hand exerting pressure directly on the bags 1 or 2, or by the bags 1 and 2 being disposed in a squeezing arrangement or being surrounded by a squeezing arrangement, preferably a commercially available pressure cuff, which can be pumped up by hand by an operator. FIG. 1 shows a pressure cuff 54 with a manually operated bellows, balloon or air pump 55 for alternately pumping up or deflating the pressure cuff 54 to compress the first bag 1 or restraighten it. In the same way, the second bag 2 is also preferably surrounded by a commercially available pressure cuff 54 which has a manually operated bellows, balloon or air pump 56 for alternately pumping up or deflating this pressure cuff 54 and thus for alternately compressing or restraightening the second bag 2. The pressure cuffs 54 are only shown diagrammatically since these are known and commercially available elements.

The two bags 1, 2, all the tubings 8, 22, 32, 40, all the hose clamps 10, 34, 42, and the two catheters 14, 46 are commercially available parts. Since no heparin is used in the removal of vessel obstructions and in the reperfusion, all surfaces coming into contact with blood, in particular the inner surfaces of the bags 1 and 2 and of the lines 8, 14, 32 and 40, must be provided with a coating of heparin.

According to the invention, the following method can be used for mixing blood and an auxiliary liquid for reperfusion of blood vessels:

First step: Introduction of blood into the first bag 1 up to a defined filling level marker 4;

Second step: Independently of the first step, and before, at the same time as or after the first step, delivery of auxiliary liquid from the container 26 for auxiliary liquid into the second bag 2 up to a predetermined filling level marker 6;

Third step: Transfer of a predetermined metered amount of blood from the first bag 1 into the second bag 2 after a predetermined metered amount of the auxiliary liquid has been earlier introduced into the second bag 2;

Fourth step: Emptying the mixture of blood and auxiliary liquid, or a metered amount of the mixture, from the second bag.

Instead of the level markers 4 and/or 6, the two bags 1 and 2 can have other means, e.g., floats or electrical elements, for displaying the level to which the bags 1 and 2 are filled. In those cases, the bags 1 and 2 need not be made of transparent or translucent material. The means for displaying the filling level are used to mix a metered amount of blood with a metered amount of the reperfusion liquid and to deliver a metered amount of such a mixture through the reperfusion catheter 46.

Figure 2:
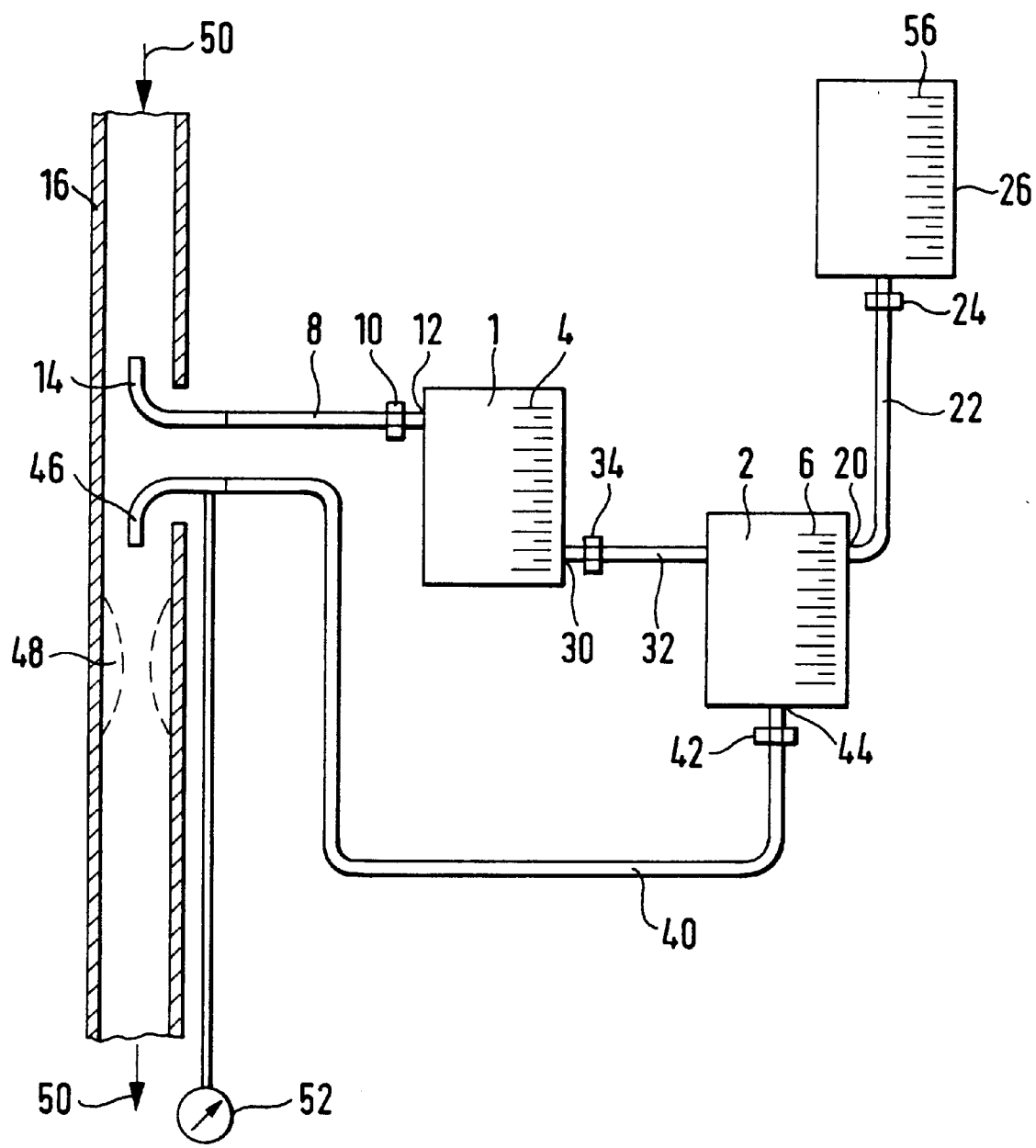
FIG. 2 is a diagrammatic representation of another embodiment of the invention.

It is possible to use bags 1 and 2 which do not have any means for displaying the filling level (4, 6 or others) if the metered amounts are otherwise definable. For example, FIG. 2 shows an embodiment in which the container 26 has means 56 which display the filling level. These enable reading off the metered amount of reperfusion liquid which is transferred from the container 26 into the second bag 2. In this case, the second bag 2 does not need any means 6 for displaying the filling level.

The container 26 can be made of transparent or translucent material, and its means 56 for displaying the filling level can be markers provided on the container.

In yet another embodiment, the first bag 1 does not need any means for displaying its filling level, e.g. 4, if at least the second bag 2, or this second bag 2 and the container 26, have such means (6, 56). In this case, blood can first be transferred from the first bag 1 into the second bag 2 through the tube 32 until a defined level has been reached in the second bag 2. Then reperfusion liquid is transferred from the container 26 into the second bag 2 until a defined second level has been reached in the second bag 2, or until the level in the container 26 has fallen to a defined value.

Since it is difficult to empty the second bag 2 completely, its filling level display 6 is not a reliable measure for accurately metered amounts. Therefore, the blood is preferably metered using filling level display means 4 of the first bag 1, and the reperfusion liquid is preferably metered using filling level display means 56 of the container 26.

It is possible for the second bag 2 to be connected to other bags of the same type in order to admix further liquids to the blood in metered amounts.

Instead of the preferred hose clamps 10, 24, 34 and 42, cocks, valves or other closure means can be used.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A reperfusion device for reperfusion of a patient's blood vessel by receiving blood from the patient, mixing the blood into a reperfusion solution in a mixing ratio and delivering the mixture into the patient's blood vessel, the reperfusion device comprising:

a first flexible bag and a second flexible bag, each being compressible for emptying the bag and being restraightenable after compressing for enabling additional filling, at least one of the bags having means for displaying a filling level of the bag;

a blood withdrawal line connected with the first bag through which blood enters the first bag from the patient, the blood withdrawal line being selectively repeatably openable and closable;

a transfer tube connecting the first bag to the second bag for transferring blood directly from the first to the second bag upon compressing the first bag, the transfer tube being selectively openable and closable;

a storage container for reperfusion liquid connected to the second bag by a supply tube connected between the storage container and the second bag for supplying reperfusion liquid to the second bag, a selectively openable and closable closure element being provided on the supply tube between the storage container and the second bag, the storage container including means for displaying a filling level of the storage container;

a reperfusion catheter connected with the second bag through a reperfusion tube for enabling delivery of a metered amount of the mixture of blood and reperfusion liquid from the second bag toward the blood vessel upon compressing the second bag, the reperfusion tube being selectively openable and closable; and a respective pressure cuff on at least one of the first and second bags, the pressure cuff being manually inflatable and deflatable respectively to compress and enable restraightening of the respective bag.

2. The reperfusion device of claim 1, further comprising closure elements for selectively closing and opening the blood withdrawal line, the tube between the first and second bags, the reperfusion catheter and the second tube connected between the second bag to the storage container.

3. The reperfusion device of claim 2, wherein the closure elements each comprise a hose clamp and the connection from the blood vessel, the tube between the bags, the reperfusion catheter and the connection of the second bag on which the closure elements are positioned are clampable hoses to be clamped by the hose clamps.

4. The reperfusion device of claim 1, wherein the storage container has a filling level display.

5. The reperfusion device of claim 1, wherein the storage container is made of a transparent or translucent material and has a filling level mark.

6. The reperfusion device of claim 1, further comprising a first meter for visual display of the metered amount of blood at the blood withdrawal line and a second meter for visual display of the metered amount of reperfusion liquid at the connection to the supply of the reperfusion liquid.

7. The reperfusion device of claim 1, wherein at least one of the bags is comprised of a transparent or translucent material enabling the filling level within bag to be visibly detectable from outside the bag.

8. The reperfusion device of claim 7, wherein the transparent or translucent material is provided with a filling level marker.

9. The reperfusion device of claim 1, wherein at least one of the bags is made of plastic and is compressible.

10. The reperfusion device of claim 1, including surfaces thereof which contact with blood which include the inner surfaces of the bags and the tubes, and these blood contacting surfaces have a coating heparin.

11. The reperfusion device of claim 1, further comprising a pressure measurement unit for visually displaying the pressure prevailing in the reperfusion catheter.

* * * * *